United States Patent [19]
Li et al.

[11] Patent Number: 5,861,272
[45] Date of Patent: Jan. 19, 1999

[54] C5A RECEPTOR

[75] Inventors: Yi Li, Gaithersburg; Craig A. Rosen, Laytonsville, both of Md.

[73] Assignee: Human Genome Sciences, Inc., Rockville, Md.

[21] Appl. No.: 458,970

[22] Filed: Jun. 2, 1995

Related U.S. Application Data

[63] Continuation-in-part of PCT/US94/09234 Aug. 16, 1994.

[51] Int. Cl.$^6$ ............................. C12P 21/02; C12N 15/85
[52] U.S. Cl. ...................... 435/69.1; 435/320.1; 536/23.5
[58] Field of Search ............................... 435/69.1, 240.2, 435/172.1, 172.3, 320.1, 325; 536/23.1, 23.5

[56] References Cited

U.S. PATENT DOCUMENTS

| | | | |
|---|---|---|---|
| 4,772,584 | 9/1988 | Cleary et al. | 514/2 |
| 5,177,190 | 1/1993 | Rollins et al. | 530/350 |
| 5,223,485 | 6/1993 | Kawai et al. | 514/16 |

FOREIGN PATENT DOCUMENTS

| | | |
|---|---|---|
| 0377489 | 7/1990 | European Pat. Off. . |
| 91/05047 | 4/1991 | WIPO . |

OTHER PUBLICATIONS

Nature, vol. 349, pp. 614–617 (Feb. 14, 1991).
J. of Biological Chem., vol. 264, No. 3, pp. 1760–1766 (Jan. 25, 1989).
Biochem. J., vol. 288, pp. 911–917 (1992).
Biochemistry, vol. 30, No. 12, pp. 2993–2999 (1991).

*Primary Examiner*—David Guzo
*Attorney, Agent, or Firm*—E. M. Olstein; J. G. Mullins

[57] ABSTRACT

A human C5a receptor polypeptide and DNA (RNA) encoding such polypeptide and a procedure for producing such polypeptide by recombinant techniques is disclosed. Also disclosed are methods for utilizing such polypeptide for identifying antagonists and agonists to such polypeptide. Antagonists and agonists may be used therapeutically to inhibit or stimulate the C5a receptor. Also disclosed are diagnostic methods for detecting mutations in the polynucleotides of the present invention and for detecting levels of the soluble polypeptides in samples derived from a host.

35 Claims, 9 Drawing Sheets

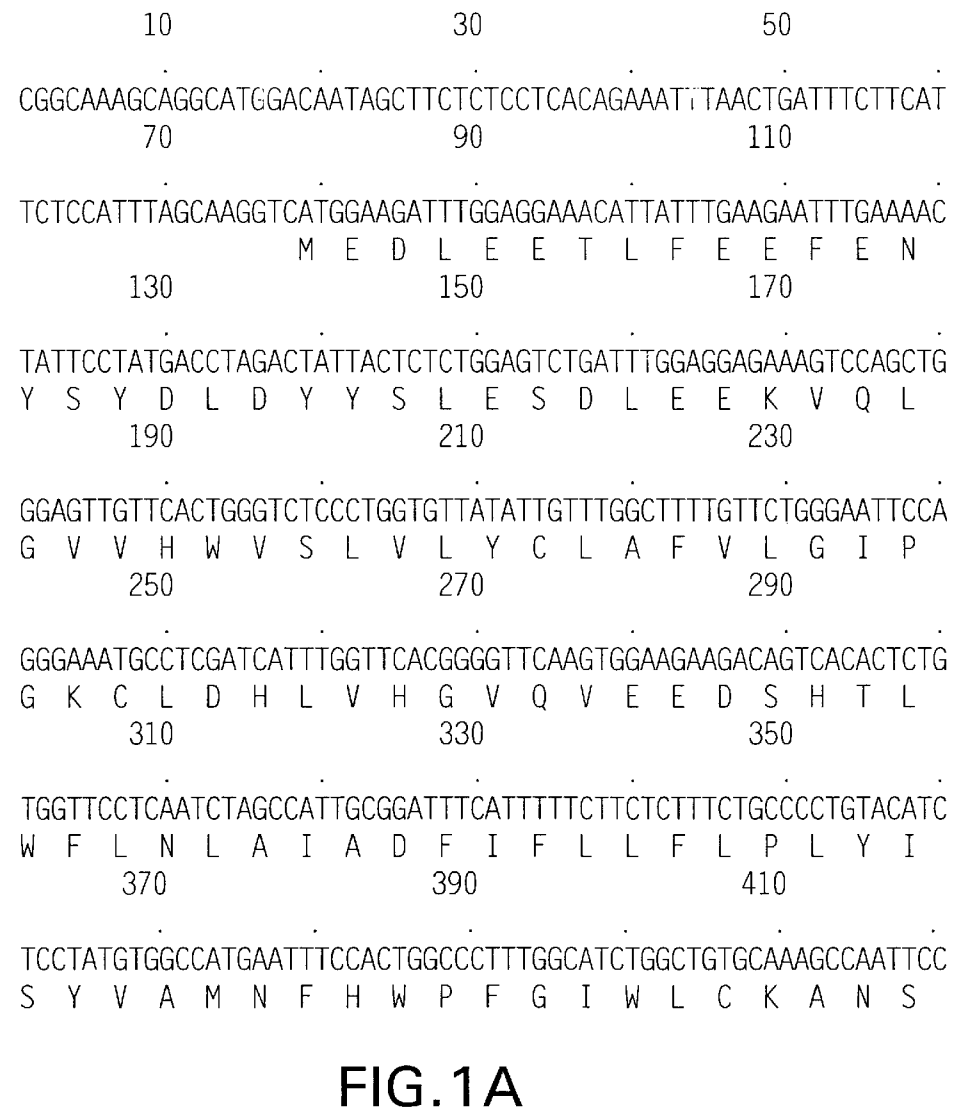

```
                                              .                     .                     .                     .                     .
CGGCAAGCAGGCATGGACAATAGCTTCTCTCCTCACAGAAAT::TAACTGATTTCTTCAT
         10                   30                    50
                                              .                     .                     .                     .                     .
                                        TCTCCATTTAGCAAGGTCATGGAAGATTTGGAGGAAAACATTATTTGAAGAATTTGAAAAC
         70                    90                   110
                                                     M   E   D   L   E   E   T   L   F   E   E   F   E   N
                                                    130                   150                   170
                                              .                     .                     .                     .                     .
TATTCCTATGACCTAGACTATTACTCTCTGGAGTCTGATTGGAGGAGAAAGTCCAGCTG
 Y   S   Y   D   L   D   Y   Y   S   L   E   S   D   L   E   E   K   V   Q   L
         190                  210                   230
                                              .                     .                     .                     .                     .
GGAGTTGTTCACTGGGTCTCCCTGGTGTTATATTGTTTGGCTTTTGTTCTGGGAATTCCA
 G   V   V   H   W   V   S   L   V   L   Y   C   L   A   F   V   L   G   I   P
         250                  270                   290
                                              .                     .                     .                     .                     .
GGGAAATGCCTCGATCATTGGTTCATGACCTTCAAGTGGAAGAAGACAGTCACACTCTG
 G   K   C   L   D   H   L   V   H   G   V   Q   V   E   E   D   S   H   T   L
         310                  330                   350
                                              .                     .                     .                     .                     .
TGGTTCCTCAATCTAGCCATTGCGGATTTCATTTTTCTTCTTTTCTGCCCTGTACATC
 W   F   L   N   L   A   I   A   D   F   I   F   L   L   F   L   P   L   Y   I
         370                  390                   410
                                              .                     .                     .                     .                     .
TCCTATGTGGCCATGAATTTCCACTGGCCCTTTGGCATCGGCTGTGCAAAGCCAATTCC
 S   Y   V   A   M   N   F   H   W   P   F   G   I   W   L   C   K   A   N   S
```

FIG.1A

```
                                                                        470
                                                      .                  .
TTCACTGCCCAGTTGAACATGTTTGCCAGTGTTTTTTCCTGACAGTGATCAGCCTGGAC
 F  T  A  Q  L  N  M  F  A  S  V  F  F  L  T  V  I  S  L  D
             490                                 510                             530

CACTATATCCACTTGATCCATCATCTGTCTTATCTCATCGGCATCGAACCCTCAAGAACTCT
 H  Y  I  H  L  I  H  P  V  L  S  H  R  H  R  T  L  K  N  S
             550                                 570                             590

CTGATTGTCATTATATTCATCTGGCTTGTGGCTTCTCTAATTGGCGGTCCTGCCCTGTAC
 L  I  V  I  I  F  I  W  L  V  A  S  L  I  G  G  P  A  L  Y
             610                                 630                             650

TTCCGGGATACTGTGGAGTTCAATAATCATACTCTTTGGTATAACAATTTTCAGAAGCAT
 F  R  D  T  V  E  F  N  N  H  T  L  W  Y  N  N  F  Q  K  H
             670                                 690                             710

GATCCTGACCTCACTTGGATCAGGCACCATGTTCTGACTTGGGTGAAATTTATCATTGGT
 D  P  D  L  T  W  I  R  H  H  V  L  T  W  V  K  F  I  I  G
             730                                 750                             770

TATCTCTTCCCTTTGCTAACAATGAGTATTCGGTACTTGTGTCTCATCTTCAAGGTGAAG
 Y  L  F  P  L  L  T  M  S  I  R  Y  L  C  L  I  F  K  V  K
             790                                 810                             830

AAGCGAAGCATCCTGATCTCCAGTAGGCATTTCTGGACAATTCTGGTTGTGGTTGTGGCC
 K  R  S  I  L  I  S  S  R  H  F  W  T  I  L  V  V  V  V  A
```

FIG. 1B

```
                                                                    .                                                                       .
                                                    TTTGTGGTTTGGTGGAACTCCTTATCACCTGTTTAGCATTGGGGAGCTCACCATTCACCAC
                                                    F  V  V  W  M  T  P  Y  H  L  F  S  I  G  E  L  T  I  H  H
           850               870             890    910                           930                           950

AATAGCTATTCCCACCATGTGATGCAGGCTGGAATCCCCTCTCCACTGGTTGGCATTC
                                                    N  S  Y  S  H  H  V  M  Q  A  G  I  P  L  S  T  G  L  A  F
                                                    970                           990                           1010

CTCAATAGTTGCTTGAACCCCATCCTTTATGTCCTAGTTAGTAAGAAGTTCCAAGCTGC
                                                    L  N  S  C  L  N  P  I  L  Y  V  L  V  S  K  K  F  Q  A  R
                                                    1030                          1050                          1070

TTCCGGTCCTCAGTTGCTGAGATACTCAAGTACACACTGTGGGAAGTCAGCTGTTCTGGC
                                                    F  R  S  S  V  A  E  I  L  K  Y  T  L  W  E  V  S  C  S  G
                                                    1090                          1110                          1130

ACAGTGAGTGAACAGCTCAGGAACTCAGAAACCAAGAATCTGTGTCTCCTGGAAACAGCT
                                                    T  V  S  E  Q  L  R  N  S  E  T  K  N  L  C  L  L  E  T  A
                                                    1150                          1170                          1180

CAATAAGTTATTACTTTTCCACAAATCAGTATATGGCTTTTTATGTGGGTCCTCTGACTG
                                                    Q  *
                                                    1210                          1230                          1250

ATGCTTTCAGATTAAAATTGTTTCCAAGATAGAGAGCCGACTCCACTTTCATAGTTATTG
```

FIG. 1C

```
                    1270              1290              1310
TTTCTGGTCACTATATAGGCATCACATTTTTGTGTGGATATGAAACTTAGGAAGGATCCT
                    1330              1350              1370
CTTGACTCCTTGTGATGTGGCAATAAATTTTTTTTAAAAAACTGAAAATACTTAGGAAGG
                    1390              1410              1430
ATCCGCATAATTTTTTCTGCAACTTAAATGAAATGCATCATTCTTGTTAATCATACCAT
                    1450              1470              1490
GGTGAATTAATCACTTTTGAAGCAATATCAGTTATTTTTTGAATAATAACTTTTCTAAAG
                    1510              1530              1550
CCTTAAGTCTTAATATTAAATATATGATTAGCCAGGCCCGGTGGCTGACACCTGTAATCC
                    1570              1590              1610
CAGCACTTTGGGAGGCCAAGGTGGGGGATTACCCGAGGTCAGGAATTCGAGACCAGCCT
                    1630              1650              1670
GACCAACATGGAGAGAAACCCGTCTCTACTAAAAATCCAAAATTAGCCGGTCATGGTGGTG
```

FIG.1D

```
                                                                    1730
                    1690                  1710
CATGTCTGCAAACCCAGCTACTCGGGAGGCTGAAGCAGGAGAATCCACTTGAACCTGGGA
                    1750                  1770                      1790

GGCAGAGGTTGTGGTGAGCCAACATCACACCATTGCACTCCAGCCTGGGCCACAAGAGTA
                    1810                  1830                      1850

AAACTCTGTCTCAAAAATAAATAAATAAATAGATAAATAAATATATGATTAACTAATTT
                    1870                  1890                      1910

TAAAAATGTTAAAAATGTATTCTTAAATTCATTTTAATTTTGTACAATAACCTGCTAGACA
                    1930                  1950                      1970

CATTTTTAAAATGCAACATGTGTACTTAATTTCTTTATGTAATCTATGTATATACATTTA
                    1990                  2010

TGAATTAAAGTAATTGTTGGTTATCTTAAAAAAAAAAAAAAAAAA
```

```
X X K X S X X L X V X D X X S L V L F A V X F    Majority
       30              40              50
L E E K V Q - L G V V H W V S L V L Y C L A F    34.PEP
V D K T S N T L R V P D I L A L V I F A V V F    HuC5aR.PEP
T Q S V S A G Y I V L D V F S Y L I F A V T F    MuFLMPR.PEP
C P K A G R H N Y I F V M I P - T L Y S I I F    HuATIIR.PEP F L N L A I A D F - - C F L L T L P L Y I X S    Majority
       80              90             100
F L N L A I A D F I - - F L L F L P L Y I S Y    34.PEP
F L N L A V A D F L S C L A - - L P I L F T S    HuC5aR.PEP
Y L N L A I A D F - - C F T S T L P F Y I A S    MuFLMPR.PEP
L L N L A L A D L - - C F L L T L P L W A V Y    HuATIIR.PEP S V F L L A X I S L D R Y L X V X H P V W S Q    Majority
      130             140             150
S V F F L T V I S L D H Y I H L I H P V L S H    34.PEP
S I L L A T I S A D R F L L V F K P I W C Q     HuC5aR.PEP
S V F L I A L I A L D R C I C V L H P V W A Q    MuFLMPR.PEP
S V F L L T C L S I D R Y L A I V H P M K S R    HuATIIR.PEP I - - - - L Y F V X N X E X X P X K T X C T F D  Majority
        180             190             200
- - - - - L Y F R D T V E F N N H - - - - - T L W  34.PEP
- - - - - L Y R V V R E E Y F P P K V L C G V D    HuC5aR.PEP
I R - - L T T V P N S R L G P G K T A C T F D    MuFLMPR.PEP
I H R N V F F I E N T N I - - - - T V C A F H    HuATIIR.PEP I L G F L F P L L I X X I C Y T L I X X K X K    Majority
      230             240             250
I I G Y L F P L L T M S I R Y L C L I F K V K    34.PEP
V L G F L W P L L T L T I C Y T F I L L R T W    HuC5aR.PEP
I I G F S T P M S I V A I C Y G L I T T K I H    MuFLMPR.PEP
I L G F L F P F L I I L T S Y T L I W K A L K    HuATIIR.PEP
```

```
X W X P Y Q V F X I X X X - I Q L X I X L X      Majority
     280              290             300
W W T P Y H L F S I G - - - - E L T I H H N      34.PEP
F W L P Y Q V T G I M M S - F - - - - - L E      HuC5aR.PEP
C W C P F Q V V A L I S T - I Q V R E R L K      MuFLMPR.PEP
S W I P H Q I F T F L D V L I Q L G I R D        HuATIIR.PEP I L Y V F X G Q K F Q X - - - R L R K S L P      Majority
     330              340             350
I L Y V L V S K K F Q A - - - R F R S S V A      34.PEP
I I Y V V A G Q G F Q G - - - R L R K S L P      HuC5aR.PEP
M L Y V F M G Q D F R E - - - R L I H S L P      MuFLMPR.PEP
L F Y G F L G K K F K R Y F L Q L L K Y I P      HuATIIR.PEP X L X X X T X X A X      Majority
     380
N L C L L E T A Q        34.PEP
- M A Q K T - Q A V      HuC5aR.PEP
S L S E N T L N A M      MuFLMPR.PEP
K K P A P C F E V E      HuATIIR.PEP
```

FIG.2B2

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2024 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

| | | | | | |
|---|---|---|---|---|---|
| CGGCAAAGCA | GGCATGGACA | ATAGCTTCTC | TCCTCACAGA | AATTAACTG | ATTTCTTCAT | 60 |
| TCTCCATTTA | GCAAGGTCAT | GGAAGATTTG | GAGGAAACAT | TATTTGAAGA | ATTTGAAAAC | 120 |
| TATTCCTATG | ACCTAGACTA | TTACTCTCTG | GAGTCTGATT | TGGAGGAGAA | AGTCCAGCTG | 180 |
| GGAGTTGTTC | ACTGGGTCTC | CCTGGTGTTA | TATTGTTTGG | CTTTTGTTCT | GGGAATTCCA | 240 |
| GGGAAATGCC | TCTATCATTT | GGTTCACGGG | GTTCAAGTGG | AAGAAGACAG | TCACACTCTG | 300 |
| TGGTTCCTCA | ATCTAGCCAT | TGCGGATTTC | ATTTTCTTC | TCTTTCTGCC | CCTGTACATC | 360 |
| TCCTATGTGG | CCATGAATTT | CCACTGGCCC | TTTGGCATCT | GGCTGTGCAA | AGCCAATTCC | 420 |
| TTCACTGCCC | AGTTGAACAT | GTTTGCCAGT | GTTTTTTCC | TGACAGTGAT | CAGCCTGGAC | 480 |
| CACTATATCC | ACTTGATCCA | TCCTGTCTTA | TCTCATCGGC | ATCGAACCCT | CAAGAACTCT | 540 |
| CTGATTGTCA | TTATATTCAT | CTGGCTTGTG | GCTTCTCTAA | TTGGCGGTCC | TGCCCTGTAC | 600 |
| TTCGGGATA | CTGTGGAGTT | CAATAATCAT | ACTCTTTGGT | ATAACAATTT | TCAGAAGCAT | 660 |
| GATCCTGACC | TCACTTGGAT | CAGGCACCAT | GTTCTGACTT | GGGTGAAATT | TATCATTGGT | 720 |
| TATCTCTTCC | CTTTGCTAAC | AATGAGTATT | CGGTACTTGT | GTCTCATCTT | CAAGGTGAAG | 780 |
| AAGCGAAGCA | TCCTGATCTC | CAGTAGGCAT | TTCTGGACAA | TTCTGGTTGT | GGTTGTGGCC | 840 |
| TTTGTGGTTT | GGTGGACTCC | TTATCACCTG | TTTAGCATTG | GGAGCTCAC | CATTCACCAC | 900 |
| AATAGCTATT | CCCACCATGT | GATGCAGGCT | GGAATCCCCC | TCTCCACTGG | TTTGGCATTC | 960 |
| CTCAATAGTT | GCTTGAACCC | CATCCTTTAT | GTCCTAGTTA | GTAAGAAGTT | CCAAGCTCGC | 1020 |
| TTCCGGTCCT | CAGTTGCTGA | GATACTCAAG | TACACACTGT | GGGAAGTCAG | CTGTTCTGGC | 1080 |

-continued

```
ACAGTGAGTG AACAGCTCAG GAACTCAGAA ACCAAGAATC TGTGTCTCCT GGAAACAGCT      1140

CAATAAGTTA TTACTTTTCC ACAAATCAGT ATATGGCTTT TTATGTGGGT CCTCTGACTG      1200

ATGCTTTCAG ATTAAAATTG TTTCCAAGAT AGAGAGCCGA CTCCACTTTC ATAGTTATTG      1260

TTTCTGGTCA CTATATAGGC ATCACATTTT TGTGTGGATA TGAAACTTAG GAAGGATCCT      1320

CTTGACTCCT TGTGATGTGG CAATAAATTT TTTTTAAAAA ACTGAAAATA CTTAGGAAGG      1380

ATCCGCATAA TTTTTTTCTG CAACTTAAAT GAAATGCATC ATTCTTGTTA ATCATACCAT      1440

GGTGAATTAA TCACTTTTGA AGCAATATCA GTTATTTTTT GAATAATAAC TTTTCTAAAG      1500

CCTTAAGTCT TAATATTAAA TATATGATTA GCCAGGCCCG GTGGCTGACA CCTGTAATCC      1560

CAGCACTTTG GGAGGCCAAG GTGGGGGGAT TACCCGAGGT CAGGAATTCG AGACCAGCCT      1620

GACCAACATG GAGAAACCCC GTCTCTACTA AAAATCCAAA ATTAGCCGGT CATGGTGGTG      1680

CATGTCTGCA AACCCAGCTA CTCGGGAGGC TGAAGCAGGA GAATCCACTT GAACCTGGGA      1740

GGCAGAGGTT GTGGTGAGCC AACATCACAC CATTGCACTC CAGCCTGGGC CACAAGAGTA      1800

AAACTCTGTC TCAAAATAA ATAAATAAAA TAGATAAATA AATATATGAT TAACTAATTT       1860

TAAAAATGTT AAAATGTATT CTTAAATTCA TTTTAATTTT GTACAATAAC CTGCTAGACA      1920

CATTTTTAAA ATGCAACATG TGTACTTAAT TTCTTTATGT AATCTATGTA TATACATTTA      1980

TGAATTAAAG TAATTGTTGG TTATCTTAAA AAAAAAAAAA AAAA                        2024
```

(2) INFORMATION FOR SEQ ID NO:2:

(i) SEQUENCE CHARACTERISTICS:
        (A) LENGTH: 355 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Met Glu Asp Leu Glu Glu Thr Leu Phe Glu Glu Phe Glu Asn Tyr
                  5                  10                  15

Ser Tyr Asp Leu Asp Tyr Tyr Ser Leu Glu Ser Asp Leu Glu Glu
                 20                  25                  30

Lys Val Gln Leu Gly Val Val His Trp Val Ser Leu Val Leu Tyr
                 35                  40                  45

Cys Leu Ala Phe Val Leu Gly Ile Pro Gly Lys Cys Leu Asp His
                 50                  55                  60

Leu Val His Gly Val Gln Val Glu Glu Asp Ser His Thr Leu Trp
                 65                  70                  75

Phe Leu Asn Leu Ala Ile Ala Asp Phe Ile Phe Leu Leu Phe Leu
                 80                  85                  90

Pro Leu Tyr Ile Ser Tyr Val Ala Met Asn Phe His Trp Pro Phe
                 95                 100                 105

Gly Ile Trp Leu Cys Lys Ala Asn Ser Phe Thr Ala Gln Leu Asn
                110                 115                 120

Met Phe Ala Ser Val Phe Phe Leu Thr Val Ile Ser Leu Asp His
                125                 130                 135

Tyr Ile His Leu Ile His Pro Val Leu Ser His Arg His Arg Thr
                140                 145                 150

Leu Lys Asn Ser Leu Ile Val Ile Ile Phe Ile Trp Leu Val Ala
                155                 160                 165
```

| Ser | Leu | Ile | Gly | Gly | Pro | Ala | Leu | Tyr | Phe | Arg | Asp | Thr | Val | Glu |
|     |     |     |     | 170 |     |     |     | 175 |     |     |     |     |     | 180 |
| Phe | Asn | Asn | His | Thr | Leu | Trp | Tyr | Asn | Asn | Phe | Gln | Lys | His | Asp |
|     |     |     |     | 185 |     |     |     |     | 190 |     |     |     |     | 195 |
| Pro | Asp | Leu | Thr | Trp | Ile | Arg | His | His | Val | Leu | Thr | Trp | Val | Lys |
|     |     |     |     | 200 |     |     |     |     | 205 |     |     |     |     | 210 |
| Phe | Ile | Ile | Gly | Tyr | Leu | Phe | Pro | Leu | Leu | Thr | Met | Ser | Ile | Arg |
|     |     |     |     | 215 |     |     |     |     | 220 |     |     |     |     | 225 |
| Tyr | Leu | Cys | Leu | Ile | Phe | Lys | Val | Lys | Lys | Arg | Ser | Ile | Leu | Ile |
|     |     |     |     | 230 |     |     |     |     | 235 |     |     |     |     | 240 |
| Ser | Ser | Arg | His | Phe | Trp | Thr | Ile | Leu | Val | Val | Val | Ala | Phe |     |
|     |     |     |     | 245 |     |     |     |     | 250 |     |     |     | 255 |     |
| Val | Val | Trp | Trp | Thr | Pro | Tyr | His | Leu | Phe | Ser | Ile | Gly | Glu | Leu |
|     |     |     |     | 260 |     |     |     |     | 265 |     |     |     |     | 270 |
| Thr | Ile | His | His | Asn | Ser | Tyr | Ser | His | His | Val | Met | Gln | Ala | Gly |
|     |     |     |     | 275 |     |     |     |     | 280 |     |     |     |     | 285 |
| Ile | Pro | Leu | Ser | Thr | Gly | Leu | Ala | Phe | Leu | Asn | Ser | Cys | Leu | Asn |
|     |     |     |     | 290 |     |     |     |     | 295 |     |     |     |     | 300 |
| Pro | Ile | Leu | Tyr | Val | Leu | Val | Ser | Lys | Lys | Phe | Gln | Ala | Arg | Phe |
|     |     |     |     | 305 |     |     |     |     | 310 |     |     |     |     | 315 |
| Arg | Ser | Ser | Val | Ala | Glu | Ile | Leu | Lys | Tyr | Thr | Leu | Trp | Glu | Val |
|     |     |     |     | 320 |     |     |     |     | 325 |     |     |     |     | 330 |
| Ser | Cys | Ser | Gly | Thr | Val | Ser | Glu | Gln | Leu | Arg | Asn | Ser | Gly | Thr |
|     |     |     |     | 335 |     |     |     |     | 340 |     |     |     |     | 345 |
| Lys | Asn | Leu | Cys | Leu | Leu | Glu | Thr | Ala | Gln |     |     |     |     |     |
|     |     |     |     | 350 |     |     |     | 355 |     |     |     |     |     |     |

( 2 ) INFORMATION FOR SEQ ID NO:3:

( i ) SEQUENCE CHARACTERISTICS:
        ( A ) LENGTH: 30 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

GACTAAAGCT TAATGGAAGA TTTGGAGGAA　　　　　　　　　　30

( 2 ) INFORMATION FOR SEQ ID NO:4:

( i ) SEQUENCE CHARACTERISTICS:
        ( A ) LENGTH: 35 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

GAACTTCTAG ACCGTTATTG AGCTGTTTCC AGGAG　　　　　　　35

( 2 ) INFORMATION FOR SEQ ID NO:5:

( i ) SEQUENCE CHARACTERISTICS:
        ( A ) LENGTH: 35 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

GTCCGAAGCT TGCCACCATG GAAGATTTGG AGGAA                                                                35

( 2 ) INFORMATION FOR SEQ ID NO:6:

( i ) SEQUENCE CHARACTERISTICS:
       ( A ) LENGTH: 61 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: Oligonucleotide ( x i ) SEQUENCE DESCRIPTION: SEQ ID NO:6:

CTAGCTCGAG TCAAGCGTAG TCTGGGACGT CGTATGGGTA GCATTGAGCT GTTTCCAGGA                      60

G                                                                                                      61

( 2 ) INFORMATION FOR SEQ ID NO:7:

( i ) SEQUENCE CHARACTERISTICS:
       ( A ) LENGTH: 33 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: Oligonucleotide ( x i ) SEQUENCE DESCRIPTION: SEQ ID NO:7:

GCCGGATCCG CCACCATGGA AGATTTGGAG GAA                                                                   33

( 2 ) INFORMATION FOR SEQ ID NO:8:

( i ) SEQUENCE CHARACTERISTICS:
       ( A ) LENGTH: 28 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: Oligonucleotide ( x i ) SEQUENCE DESCRIPTION: SEQ ID NO:8:

GCCGGATCCG TTATTGAGCT GTTTCCAG                                                                        28

( 2 ) INFORMATION FOR SEQ ID NO:9:

( i ) SEQUENCE CHARACTERISTICS:
       ( A ) LENGTH: 350 amino acids
       ( B ) TYPE: amino acid
       ( C ) STRANDEDNESS:
       ( D ) TOPOLOGY: linear ( i i ) MOLECULE TYPE: protein ( x i ) SEQUENCE DESCRIPTION: SEQ ID NO:9:

```
Met  Asn  Ser  Phe  Asn  Tyr  Thr  Thr  Pro  Asp  Tyr  Gly  His  Tyr  Asp  Asp
                         5                        10                       15

Lys  Asp  Thr  Leu  Asp  Leu  Asn  Thr  Pro  Val  Asp  Lys  Thr  Ser  Asn  Thr
                    20                       25                       30

Leu  Arg  Val  Pro  Asp  Ile  Leu  Ala  Leu  Val  Ile  Phe  Ala  Val  Val  Phe
               35                       40                       45

Leu  Val  Gly  Val  Leu  Gly  Asn  Ala  Leu  Val  Val  Trp  Val  Thr  Ala  Phe
          50                       55                       60

Glu  Ala  Lys  Arg  Thr  Ile  Asn  Ala  Ile  Trp  Phe  Leu  Asn  Leu  Ala  Val
 65                       70                       75                       80
```

| | | | | | | | | | | | | | | |
|---|---|---|---|---|---|---|---|---|---|---|---|---|---|---|
|Ala|Asp|Phe|Leu|Ser<br>85|Cys|Leu|Ala|Leu|Pro<br>90|Ile|Leu|Phe|Thr|Ser<br>95|Ile|
|Val|Gln|His|His<br>100|His|Trp|Pro|Phe|Gly<br>105|Ala|Ala|Cys|Ser<br>110|Ile|Leu|
|Pro|Ser|Leu<br>115|Ile|Leu|Leu|Asn|Met<br>120|Tyr|Ala|Ser|Ile|Leu<br>125|Leu|Ala|
|Thr|Ile<br>130|Ser|Ala|Asp|Arg|Phe<br>135|Leu|Leu|Val|Phe|Lys<br>140|Pro|Ile|Trp|Cys|
|Gln<br>145|Asn|Phe|Arg|Gly|Ala<br>150|Gly|Leu|Ala|Trp|Ile<br>155|Ala|Cys|Ala|Val|Ala<br>160|
|Trp|Gly|Leu|Ala|Leu<br>165|Leu|Leu|Thr|Ile|Pro<br>170|Ser|Phe|Leu|Tyr|Arg<br>175|Val|
|Val|Arg|Glu|Glu<br>180|Tyr|Phe|Pro|Pro|Lys<br>185|Val|Leu|Cys|Gly|Val<br>190|Asp|Tyr|
|Ser|His|Asp<br>195|Lys|Arg|Arg|Glu|Arg<br>200|Ala|Val|Ala|Ile|Val<br>205|Arg|Leu|Val|
|Leu|Gly<br>210|Phe|Leu|Trp|Pro|Leu<br>215|Leu|Thr|Leu|Thr|Ile<br>220|Cys|Tyr|Thr|Phe|
|Ile<br>225|Leu|Leu|Arg|Thr|Trp<br>230|Ser|Arg|Arg|Ala|Thr<br>235|Arg|Ser|Thr|Lys|Thr<br>240|
|Leu|Lys|Val|Val|Val<br>245|Ala|Val|Val|Ala|Ser<br>250|Phe|Phe|Ile|Phe|Trp<br>255|Leu|
|Pro|Tyr|Gln|Val<br>260|Thr|Gly|Ile|Met|Met<br>265|Ser|Phe|Leu|Glu|Pro<br>270|Ser|Ser|
|Pro|Thr|Phe<br>275|Leu|Leu|Leu|Asn|Lys<br>280|Leu|Asp|Ser|Leu|Cys<br>285|Val|Ser|Phe|
|Ala|Tyr<br>290|Ile|Asn|Cys|Cys|Ile<br>295|Asn|Pro|Ile|Ile|Tyr<br>300|Val|Val|Ala|Gly|
|Gln<br>305|Gly|Phe|Gln|Gly|Arg<br>310|Leu|Arg|Lys|Ser|Leu<br>315|Pro|Ser|Leu|Leu|Arg<br>320|
|Asn|Val|Leu|Thr|Glu<br>325|Glu|Ser|Val|Val|Arg<br>330|Glu|Ser|Lys|Ser|Phe<br>335|Thr|
|Arg|Ser|Thr|Val<br>340|Asp|Thr|Met|Ala|Gln<br>345|Lys|Thr|Gln|Ala|Val<br>350| | |

( 2 ) INFORMATION FOR SEQ ID NO:10:

( i ) SEQUENCE CHARACTERISTICS:
        ( A ) LENGTH: 364 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
|Met|Asp|Thr|Asn|Met<br>5|Ser|Leu|Leu|Met|Asn<br>10|Lys|Ser|Ala|Val|Asn<br>15|Leu|
|Met|Asn|Val|Ser|Gly<br>20|Ser|Thr|Gln|Ser<br>25|Val|Ser|Ala|Gly|Tyr<br>30|Ile|Val|
|Leu|Asp|Val<br>35|Phe|Ser|Tyr|Leu|Ile<br>40|Phe|Ala|Val|Thr|Phe<br>45|Val|Leu|Gly|
|Val|Leu<br>50|Gly|Asn|Gly|Leu|Val<br>55|Ile|Trp|Val|Ala|Gly<br>60|Phe|Arg|Met|Lys|
|His<br>65|Thr|Val|Thr|Thr|Ile<br>70|Ser|Tyr|Leu|Asn|Leu<br>75|Ala|Ile|Ala|Asp|Phe<br>80|

| | | | | | | | | | | | | | | |
|---|---|---|---|---|---|---|---|---|---|---|---|---|---|---|
|Cys|Phe|Thr|Ser|Thr<br>85|Leu|Pro|Phe|Tyr|Ile<br>90|Ala|Ser|Met|Val|Met<br>95|Gly|
|Gly|His|Trp|Pro<br>100|Phe|Gly|Trp|Phe|Met<br>105|Cys|Lys|Phe|Ile|Tyr<br>110|Thr|Val|
|Ile|Asp|Ile<br>115|Asn|Leu|Phe|Gly|Ser<br>120|Val|Phe|Leu|Ile|Ala<br>125|Leu|Ile|Ala|
|Leu|Asp<br>130|Arg|Cys|Ile|Cys|Val<br>135|Leu|His|Pro|Val|Trp<br>140|Ala|Gln|Asn|His|
|Arg<br>145|Thr|Val|Ser|Leu|Ala<br>150|Lys|Lys|Val|Ile|Ile<br>155|Val|Pro|Trp|Ile|Cys<br>160|
|Ala|Phe|Leu|Leu|Thr<br>165|Leu|Pro|Val|Ile|Ile<br>170|Arg|Leu|Thr|Thr|Val<br>175|Pro|
|Asn|Ser|Arg|Leu<br>180|Gly|Pro|Gly|Lys|Thr<br>185|Ala|Cys|Thr|Phe|Asp<br>190|Phe|Ser|
|Pro|Trp|Thr<br>195|Lys|Asp|Pro|Val|Glu<br>200|Lys|Arg|Lys|Val|Ala<br>205|Val|Thr|Met|
|Leu|Thr<br>210|Val|Arg|Gly|Ile|Ile<br>215|Arg|Phe|Ile|Ile|Gly<br>220|Phe|Ser|Thr|Pro|
|Met<br>225|Ser|Ile|Val|Ala|Ile<br>230|Cys|Tyr|Gly|Leu|Ile<br>235|Thr|Thr|Lys|Ile|His<br>240|
|Arg|Gln|Gly|Leu|Ile<br>245|Lys|Ser|Ser|Arg|Pro<br>250|Leu|Arg|Val|Leu|Ser<br>255|Phe|
|Val|Val|Ala|Ala<br>260|Phe|Phe|Leu|Cys|Trp<br>265|Cys|Pro|Phe|Gln|Val<br>270|Val|Ala|
|Leu|Ile|Ser<br>275|Thr|Ile|Gln|Val|Arg<br>280|Glu|Arg|Leu|Lys|Asn<br>285|Met|Thr|Pro|
|Gly|Ile<br>290|Val|Thr|Ala|Leu|Lys<br>295|Ile|Thr|Ser|Pro|Leu<br>300|Ala|Phe|Phe|Asn|
|Ser<br>305|Cys|Leu|Asn|Pro|Met<br>310|Leu|Tyr|Val|Phe|Met<br>315|Gly|Gln|Asp|Phe|Arg<br>320|
|Glu|Arg|Leu|Ile|His<br>325|Ser|Leu|Pro|Ala|Ser<br>330|Leu|Glu|Arg|Ala|Leu<br>335|Thr|
|Glu|Asp|Ser|Ala<br>340|Gln|Thr|Ser|Asp|Thr<br>345|Gly|Thr|Asn|Leu|Gly<br>350|Thr|Asn|
|Ser|Thr|Ser<br>355|Leu|Ser|Glu|Asn|Thr<br>360|Leu|Asn|Ala|Met| | | | |

( 2 ) INFORMATION FOR SEQ ID NO:11:

( i ) SEQUENCE CHARACTERISTICS:
        ( A ) LENGTH: 358 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
|Ile|Leu|Asn|Ser|Ser<br>5|Thr|Glu|Asp|Gly|Ile<br>10|Lys|Arg|Ile|Gln|Asp<br>15|Asp|
|Cys|Pro|Lys|Ala<br>20|Gly|Arg|His|Asn|Tyr<br>25|Ile|Phe|Val|Met|Ile<br>30|Pro|Thr|
|Leu|Tyr|Ser<br>35|Ile|Ile|Phe|Val|Val<br>40|Gly|Ile|Phe|Gly|Asn<br>45|Ser|Leu|Val|
|Val|Ile<br>50|Val|Ile|Tyr|Phe|Tyr<br>55|Met|Lys|Leu|Lys|Thr<br>60|Val|Ala|Ser|Val|

| | | | | | | | | | | | | | | |
|---|---|---|---|---|---|---|---|---|---|---|---|---|---|---|
| Phe 65 | Leu | Leu | Asn | Leu | Ala 70 | Leu | Ala | Asp | Leu | Cys 75 | Phe | Leu | Thr | Leu 80 |
| Pro | Leu | Trp | Ala | Val 85 | Tyr | Thr | Ala | Met | Glu 90 | Tyr | Arg | Trp | Pro | Phe 95 | Gly |
| Asn | Tyr | Leu | Cys 100 | Lys | Ile | Ala | Ser | Ala 105 | Ser | Val | Ser | Phe | Asn 110 | Leu | Tyr |
| Ala | Ser | Val 115 | Phe | Leu | Leu | Thr | Cys 120 | Leu | Ser | Ile | Asp | Arg 125 | Tyr | Leu | Ala |
| Ile | Val 130 | His | Pro | Met | Lys | Ser 135 | Arg | Leu | Arg | Arg | Thr 140 | Met | Leu | Val | Ala |
| Lys 145 | Val | Thr | Cys | Ile | Ile 150 | Ile | Trp | Leu | Leu | Ala 155 | Gly | Leu | Ala | Ser | Leu 160 |
| Pro | Ala | Ile | Ile | His 165 | Arg | Asn | Val | Phe | Phe 170 | Ile | Glu | Asn | Thr | Asn 175 | Ile |
| Thr | Val | Cys | Ala 180 | Phe | His | Tyr | Glu | Ser 185 | Gln | Asn | Ser | Thr | Leu 190 | Pro | Ile |
| Gly | Leu | Gly 195 | Leu | Thr | Lys | Asn | Ile 200 | Leu | Gly | Phe | Leu | Phe 205 | Pro | Phe | Leu |
| Ile | Ile 210 | Leu | Thr | Ser | Tyr | Thr 215 | Leu | Ile | Trp | Lys | Ala 220 | Leu | Lys | Lys | Ala |
| Tyr 225 | Glu | Ile | Gln | Lys | Asn 230 | Lys | Pro | Arg | Asn | Asp 235 | Asp | Ile | Phe | Lys | Ile 240 |
| Ile | Met | Ala | Ile | Val 245 | Leu | Phe | Phe | Phe | Phe 250 | Ser | Trp | Ile | Pro | His 255 | Gln |
| Ile | Phe | Thr | Phe 260 | Leu | Asp | Val | Leu | Ile 265 | Gln | Leu | Gly | Ile | Ile 270 | Arg | Asp |
| Cys | Arg | Ile 275 | Ala | Asp | Ile | Val | Asp 280 | Thr | Ala | Met | Pro | Ile 285 | Thr | Ile | Cys |
| Ile | Ala 290 | Tyr | Phe | Asn | Asn | Cys 295 | Leu | Asn | Pro | Leu | Phe 300 | Tyr | Gly | Phe | Leu |
| Gly 305 | Lys | Lys | Phe | Lys | Arg 310 | Tyr | Phe | Leu | Gln | Leu 315 | Leu | Lys | Tyr | Ile | Pro 320 |
| Pro | Lys | Ala | Lys | Ser 325 | His | Ser | Asn | Leu | Ser 330 | Thr | Lys | Met | Ser | Thr 335 | Leu |
| Ser | Tyr | Arg | Pro 340 | Ser | Asp | Asn | Val | Ser 345 | Ser | Ser | Thr | Lys | Lys 350 | Pro | Ala |
| Pro | Cys | Phe 355 | Glu | Val | Glu | | | | | | | | | | |

C5A RECEPTOR

This application is a continuation-in-part of a previous application filed under the Patent Cooperation Treaty on Aug. 16, 1994 and assigned Ser. No. PCT/US94/09234.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as an anaphylatoxin C5a receptor, sometimes hereinafter referred to as "C5a". The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

A wide variety conditions, including infection by bacteria, viruses or fungi, infiltration by cancer cells, allergic or autoimmune disorders and physically or chemically-induced trauma causes an inflammatory response in humans. In all of these diseases and conditions in man and in most mammals, activation of the complement system (a set of proteins, regulatory factors and proteolytic enzymes) via either the classical or the alternative pathway results in the generation of biologically active peptides which serve to amplify and exacerbate the resulting inflammation.

The most active peptide, anaphylatoxin C5a, a 74-amino acid polypeptide, is generated by cleavage of the alpha-chain of native C5 at a specific site by convertase of the blood complement system, as well as by enzymes of the coagulation system. In vivo, C5a is thought to play a significant role in the inflammatory response and in a number of clinical disorders (Goldstein, I. M., Inflammation: Basic Principles and Clinical Correlates, 309–323, Raven Press, New York (1988)). This peptide is a highly potent inflammatory agent, evoking dramatic responses in experimental animals (Bodammer, G. and Vogt, W., Int. Arch. Allergy Appl. Immunol., 33:417–428 (1967)), and stimulating pulmonary, cardiac, vascular and gastrointestinal tissues in vitro (Stimler, N. P., et al., Am. J. Pathol., 100:327–348 (1980)). C5a is a potent activator of polymorphonuclear neutrophils and macrophages, stimulating chemotaxis, hydrolytic enzyme release, and superoxide anion formation (Ward, P. A. and Newman, L. J., J. Immunol., 102:93–99 (1969)). Several reports have additionally demonstrated actions of this peptide on eosinophils, including chemotaxis and increased hexose uptake, in addition to its actions on mast cells and basophils (Hugli, T. E., Biological Response Mediators and Modulators, 99–116, Academic Press, New York (1983)). In addition, the anaphylatoxin has been shown to have a spasmogenic effect on various tissues; it stimulates smooth muscle contraction (Stimler, N. P., et al., J. Immunol., 126:2258–2261 (1981)); induces histamine release from mast cells, promotes serotonin release from platelets (Meuer, S., et al., J. Immunol., 126:1506–1509 (1981)), and increases vascular permeability (Jose, P. J., et al., J. Immunol., 127:2376–2380 (1981)).

The responses elicited by C5a in polymorphonuclear leukocytes result from the winding of the anaphylatoxin to a high-affinity receptor on the plasma membrane (Chenoweth, D. E. and Hugli, T. E., Mol. Immunol., 17:151–161 (1980)). In these cells, it appears that the mechanism of signal transduction through the membrane involves one or more GTP-binding proteins (G proteins) as is the case with other chemotactic receptors. The receptor molecule for C5a on human neutrophils has been well characterized with respect to its kinetics and saturability and many of the structural requirements for its activity are known. Reports indicate that the neutrophil C5a receptor binds its ligand with a nanomolar affinity constant, is expressed in approximately 100,000 copies per cell, and the binding sub-unit has an apparent mass of approximately 52 kDa.

The interaction of C5a with polymorphonuclear leukocytes and other target cells and tissues results in increased histamine release, vascular permeability, smooth muscle contraction, and an influx into tissues of inflammatory cells, including neutrophils, eosinophils and basophils (Hugli, T. E., Springer, Semin. Immunopathol., 7:193–219 (1981)). C5a may also play an important role in mediating inflammatory effects of phagocytic mononuclear cells that accumulate at sites of chronic inflammation (Allison, A. C., et al., H. U. Agents and Actions, 8:27 (1978)). C5a can induce chemotaxis in monocytes and cause them to release lysosomal enzymes in a manner analogous to the neutrophil responses elicited by these agents. C5a may have an immunoregulatory role by enhancing antibody, particularly as sites of inflammation (Morgan, E. L., et al., J. Exp. Med., 155:1412 (1982)).

In accordance with one aspect of the present invention, there are provided novel polypeptides, as well as fragments, analogs and derivatives thereof. The polypeptides of the present invention are of human origin.

In accordance with another aspect of the present invention, there are provided polynucleotides (DNA or RNA) which encode such polypeptides.

In accordance with a further aspect of the present invention, there is provided a process for producing such polypeptides by recombinant techniques.

In accordance with yet a further aspect of the present invention, there are provided antibodies against such polypeptides.

In accordance with another embodiment, there is provided a process for using the receptor to screen for receptor antagonists and/or agonists and/or receptor ligands.

In accordance with still another embodiment of the present invention there is provided a process of using such agonists for therapeutic purposes, for example, as a defense against bacterial infection, to stimulate the immunoregulatory effects of C5a, to treat cancers, immunodeficiency diseases and severe infections.

In accordance with another aspect of the present invention there is provided a process of using such antagonists for treating asthma, bronchial allergy, chronic inflammation, systemic lupus erythematosis, vasculitis, rheumatoid arthritis, osteoarthritis, gout, some auto-allergic diseases, transplant rejection, ulcerative colitis, in certain shock states, myocardial infarction, and post-viral encephalopathies.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1E, collectively, show the cDNA sequence (SEQ ID NO:2) and the corresponding deduced amino acid sequence (SEQ ID NO:1) of the putative mature G-protein coupled receptor of the present invention. The standard one-letter abbreviation for amino acids is used.

Figure 2A1:
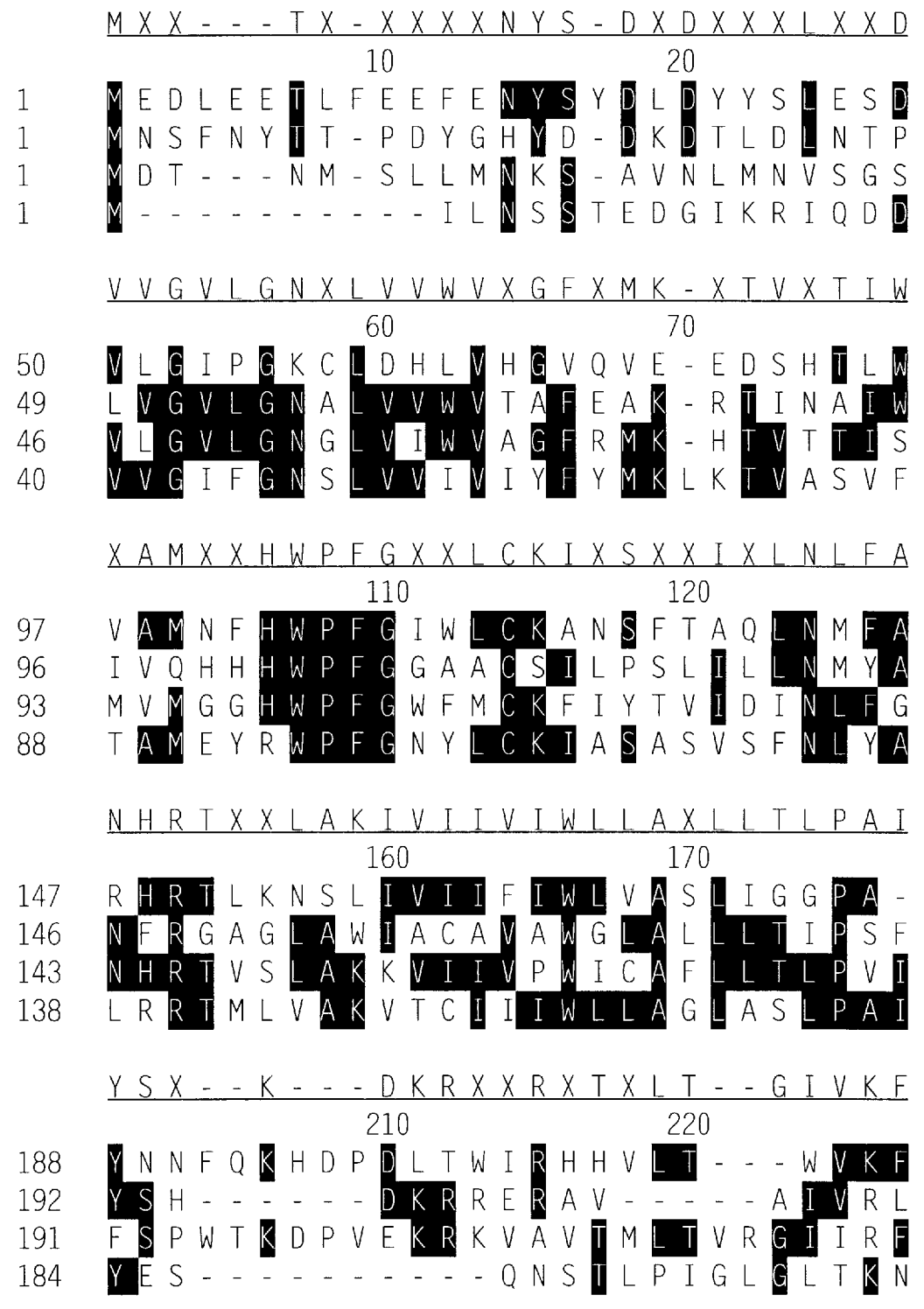
Figure 2B1:
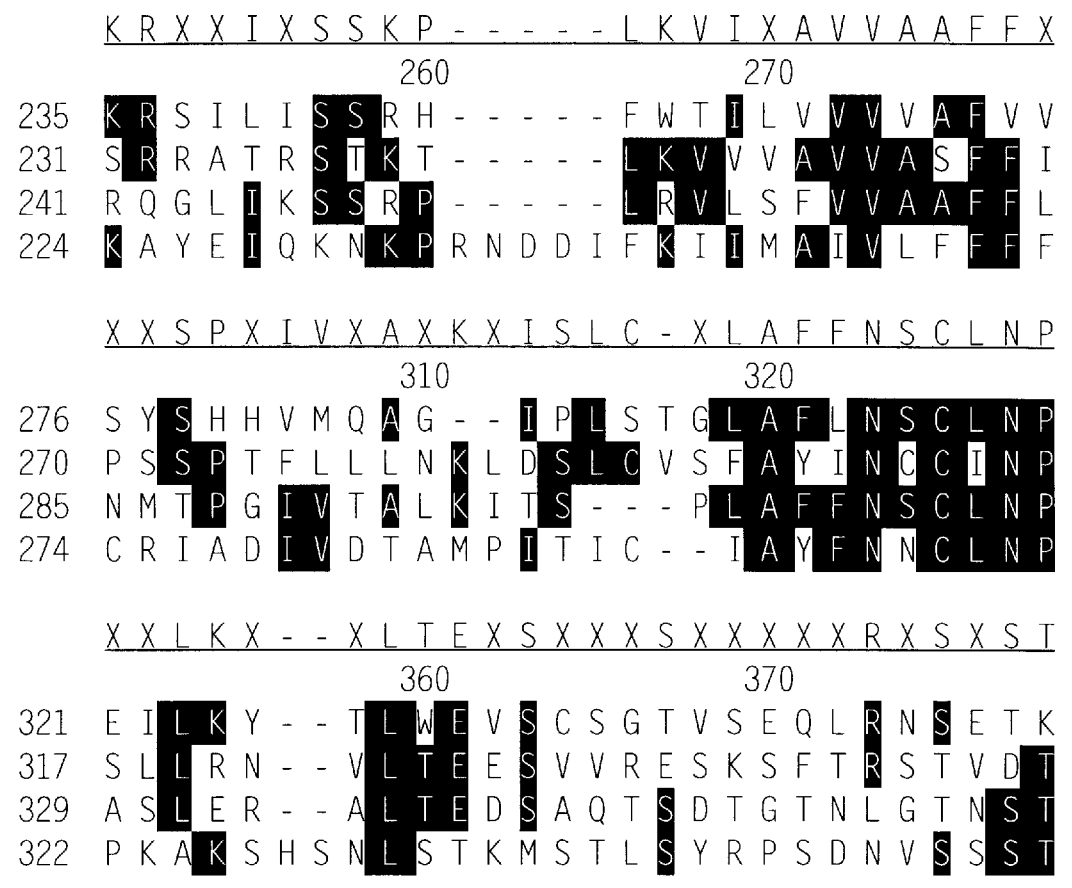

FIGS. 2A1, 2A2, 2B1 and 2B2, collectively, illustrate an amino acid alignment of the G-protein coupled receptor of the present invention and C5a receptors (SEQ ID NO:9,10 and 11) from various species of animals. Faded areas are those areas which match with the other amino acid sequences in the figure. The portions of the amino acid sequence (of SEQ ID NO:2) shown in the first comparative line of FIG. 2 and the comparative amino acid sequences (SEQ ID NOS:9–11, respectively) shown at comparative lines 2–4 of FIG. 2 are represented by the one-letter amino acid codes.

It should be pointed out that sequencing inaccuracies are a common problem which occurs in polynucleotide sequences. Accordingly, the sequence of the drawing is based on several sequencing runs and the sequencing accuracy is considered to be at least 97%.

In accordance with an aspect of the present invention, there is provided an isolated nucleic acid (polynucleotide) which encodes for the mature polypeptide having the deduced amino acid sequence of FIGS. 1A–1E, collectively, (SEQ ID NO:2) or for the mature polypeptide encoded by the cDNA of the clone deposited as ATCC Deposit No. 75821 on Jun. 24, 1994.

The deposit is a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

A polynucleotide encoding a polypeptide of the present invention is predominantly expressed in peripheral lymphocytes. The polynucleotide of this invention was discovered in a cDNA library derived from human osteoclastoma stromal cells. It is structurally related to the G protein-coupled receptor family. It contains an open reading frame encoding a protein of 355 amino acid residues. The protein exhibits the highest degree of homology to a human C5a receptor with 27% identity and 54% similarity over the entire amino acid sequence.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1E, collectively, (SEQ ID NO:1) or that of the deposited clone or may be a different coding sequence which coding sequence, as a result of the redundancy or degeneracy of the genetic code, encodes the same mature polypeptide as the DNA of FIGS. 1A–1E, collectively, (SEQ ID NO:1) or the deposited cDNA.

The polynucleotide which encodes for the mature polypeptide of FIGS. 1A–1E, collectively, (SEQ ID NO:2) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1E, collectively, (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1E, collectively, (SEQ ID NO:2) or the same mature polypeptide encoded by the cDNA of the deposited clone as well as variants of such polynucleotides which variants encode for a fragment, derivative or analog of the polypeptide of FIGS. 1A–1E, collectively, (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1E, collectively, (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1E, collectively, (SEQ ID NO:1) or the deposited cDNA (s), i.e. function as a soluble receptor by retaining the ability to bind the ligands for the receptor even though the polypeptide does not function as a membrane bound receptor, for example, by eliciting a second messenger response.

Alternatively, the polynucleotides may have at least 20 bases, preferably 30 bases and more preferably at least 50 bases which hybridize to a polynucleotide of the present invention and which have an identity thereto, as hereinabove described, and which may or may not retain activity. For example, such polynucleotides may be employed as probes for the polynucleotide of SEQ ID NO: 1, or for variants thereof, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

Fragments of the genes may be employed as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a receptor polypeptide which has the deduced amino acid sequence of FIGS. 1A–1E, collectively, (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1E, collectively, (SEQ ID NO:2) or that encoded by the deposited cDNA, means a polypeptide which either retains substantially the same biological function or activity as such polypeptide, i.e. functions as a receptor, or retains the ability to bind the ligand for the receptor even though the polypeptide does not function as a G-protein coupled receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1E, collectively, (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably a 95% identity) to the polypeptide of SEQ ID NO:2 and also includes portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAS derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The G-protein coupled receptor of the present invention may be employed in a process for screening for antagonists and/or agonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of the melanophores which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptor into xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

A potential antagonist is an antibody, or in some cases an oligonucleotide, which binds to the G-protein coupled receptor but does not elicit a second messenger response such that the activity of the G-protein coupled receptor is prevented. Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the MRNA in vivo and blocks translation of the mRNA molecule into the G-protein coupled receptors (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptors.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble form of a G-protein coupled receptor, e.g. a fragment of the receptor, which binds to the ligand and prevents the ligand from interacting with membrane bound G-protein coupled receptors.

The G-protein coupled receptor of the present invention has been putatively identified as a C5a receptor. This identification has been made as a result of amino acid sequence homology.

The antagonists may be used to treat all pathological conditions which result from anaphylaxis stimulated by the C5a polypeptide and mediated by the C5a receptor. These pathological conditions include asthma, bronchial allergy, chronic inflammation, systemic lupus erythematosus, vasculitis, serum sickness, angioedema, rheumatoid arthritis, osteoarthritis, gout, bullous skin diseases, hypersensivity, pneumonitis, idiopathic pulmonary fibrosis, immune complex-mediated glomerulonephritis, psoriasis, allergic rhinitis, adult respiratory distress syndrome, acute pulmonary disorders, endotoxin shock, hepatic cirrhosis, pancreatitis, inflammatory bowel diseases (including Crohn's disease and ulcerative colitis), thermal injury, gram-negative sepsis, necrosis in myocardial infarction, leukophoresis, exposure to medical devices (including, but not limited to, hemodialyzer membranes and extracorpeal blood circulation equipment), chronic hepatitis, transplant rejection, post-viral encephalopathies, and/or ischemia induced myocardial or brain injury. These antagonist may also be used as prophylactics for such conditions as shock accompanying Deng Urea fever. The antagonists may be employed in a composition with a pharmaceutically acceptable carrier, e.g., as hereinafter described.

The agonists identified by the screening method as described above, may be employed to enhance the C5a reactions mediated through the C5a receptor, which include defense against bacterial infection, stimulation of the immunoregulatory effects of C5a, treatment of cancers, immunodeficiency diseases and severe infections.

The C5a receptor and antagonists or agonists may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or compounds of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The C5a receptor polypeptides and antagonists or agonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total MRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of C5a Receptor

The DNA sequence encoding the C5a receptor, ATCC # 75821, is initially amplified using PCR oligonucleotide primers corresponding to the 5' end sequences of the processed C5a receptor protein (minus the signal peptide sequence) and the vector sequences 3' to the gene. Additional nucleotides corresponding to the C5a receptor were added to the 5' and 3' sequences respectively. The 5' oligonucleotide primer has the sequence 5' GACTAAAGCT-TAATGGAAGATTTGGAGGAA 3' (SEQ ID NO:3) contains a HindIII restriction enzyme site followed by 19 nucleotides of C5a receptor coding sequence starting from the presumed terminal amino acid of the processed protein codon. The 3' sequence 5' GAACTTCTAGACCGTTAT-TGAGCTGTTTCCAGGAG 3' (SEQ ID NO:4) contains complementary sequences to an XbaI site and is followed by 18 nucleotides of the gene. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with HindIII and XbaI. The amplified sequences were ligated into pQE-9 and were inserted in frame with the sequence encoding for the histidine tag and the RBS. The ligation mixture was then used to transform E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized C5a receptor was purified from this solution by chromatography on a Nickel-Chelate column under conditions that allow for tight binding by proteins containing the 6-His tag. Hochuli, E. et al., J. Chromatography 411:177–184 (1984). The C5a receptor was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant C5a Receptor in COS cells

The expression of plasmid, pC5a HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire pC5a protein and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for the C5a receptor, ATCC #75821, was constructed by PCR on the full-length gene cloned using two primers: the 5' primer 5' GTCCGAAGCT-TGCCACCATGGAA GATTTGGAGGAA 3' (SEQ ID NO:5) contains a HindIII site followed by 18 nucleotides of C5a receptor coding sequence starting from the initiation codon; the 3' sequence 5' CTAGCTCGAGTCAAGCG-TAGTCTGGGACGTCGTATGGGTAGCAT-TGAGCTGTTTCCAGGAG 3' (SEQ ID NO:6) contains complementary sequences to an XhoI site, translation stop codon, HA tag and the last 18 nucleotides of the C5a receptor coding sequence (not including the stop codon). Therefore, the PCR product contains a HindIII site, C5a receptor coding sequence followed by HA tag fused in frame, a translation termination stop codon next to the HA tag, and an XhoI site. The PCR amplified DNA fragment and the vector, pcDNAI/Amp, were digested with HindIII and XhoI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant C5a receptor, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the C5a receptor HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3
Cloning and expression of C5a receptor using the baculovirus expression system The DNA sequence encoding the full length C5a receptor protein, ATCC #75821, was amplified using PCR oligonucleotide primers corresponding to the 5' and 3' sequences of the gene:

The 5' primer has the sequence 5' GCCGGATCCGCCA CC<u>ATG</u>GAAGATTTGGAGGAA 3' (SEQ ID NO:7) and contains a BamHI restriction enzyme site (in bold) followed by 6 nucleotides resembling an efficient signal for the initiation of translation in eukaryotic cells (J. Mol. Biol. 1987, 196, 947–950, Kozak, M.), and is just behind the first 18 nucleotides of the gene (the initiation codon for translation "ATG" is underlined).

The 3' primer has the sequence 5' GCCGGATCCGT TATTGAGCTGTTTCCAG 3' (SEQ ID NO:8) and contains the cleavage site for the restriction endonuclease BamHI and 18 nucleotides complementary to the 3' non-translated sequence of the C5a receptor gene. The amplified sequences were isolated from a 1% agarose gel using a commercially available kit ("Geneclean," BIO 101 Inc., La Jolla, Calif.). The fragment was then digested with the endonucleases BamHI and then isolated again on a 1% agarose gel. This fragment is designated F2.

The vector pRG1 (modification of pVL941 vector, discussed below) is used for the expression of the C5a receptor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and then dephosphorylated using calf intestinal phosphatase by procedures known in the art. The DNA was then isolated from a 1% agarose gel as described above. This vector DNA is designated V2.

Fragment F2 and the dephosphorylated plasmid V2 were ligated with T4 DNA ligase. *E.coli* HB101 cells were then transformed and bacteria identified that contained the plasmid (pBacC5a) with the C5a receptor gene using the enzyme BamHI. The sequence of the cloned fragment was confirmed by DNA sequencing.

5 µg of the plasmid pBacC5a was co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacC5a were mixed in a sterile well of a microtiter plate containing 50 µl of serum free Grace's medium (Life Technologies Inc., Gaithersburg, Md.). Afterwards 10 µl Lipofection plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-C5a at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 4
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least a 95% identity to a member selected from the group consisting of:
   (a) a polynucleotide encoding the mature human C5A receptor protein comprisinq amino acids 2 to 355 of SEQ ID NO:2; and
   (b) the complement of (a).

2. The isolated polynucleotide of claim 1 wherein said member is (a).

3. The isolated polynucleotide of claim 1 wherein said member is (a) and said polynucleotide encodes a polypeptide comprising amino acids 2 to 355 of SEQ ID NO:2.

4. A method of making a recombinant vector comprising inserting the isolated polynucleotide of claim 1 into a vector, wherein said polynucleotide is DNA.

5. The isolated polynucleotide of claim 1 comprising nucleotides 82 to 1143 of SEQ ID NO:1.

6. The isolated polynucleotide of claim 1 comprising nucleotides 79 to 1327 of SEQ ID NO:1.

7. The isolated polynucleotide of claim 1 comprising the polynucleotide of SEQ ID NO:1.

8. The isolated polynucleotide of claim 2, wherein the polynucleotide is DNA.

9. The isolated polynucleotide of claim 2, comprising a polynucleotide encoding a polypeptide comprising an amino acid sequence identical to amino acids 1 to 355 of SEQ ID NO:2.

10. A recombinant vector comprising the polynucleotide of claim 2, wherein said polynucleotide is DNA.

11. A recombinant host cell comprising the polynucleotide of claim 2, wherein said polynucleotide is DNA.

12. The isolated polynucleotide of claim 3 wherein said member is (a) and said polypeptide comprises amino acids 1 to 355 of SEQ ID NO:2.

13. The isolated polynucleotide of claim 3, wherein the polynucleotide is DNA.

14. A recombinant vector comprising the polynucleotide of claim 8, wherein said polynucleotide is DNA.

15. A recombinant host cell comprising the polynucleotide of claim 8, wherein said polynucleotide is DNA.

16. The isolated polynucleotide of claim 13 comprising a polynucleotide encoding a polypeptide comprising an amino acid sequence identical to amino acids 1 to 355 of SEQ ID NO:2.

17. A recombinant vector comprising the polynucleotide of claim 13.

18. A recombinant host cell comprising the polynucleotide of claim 13, wherein said polynucleotide is DNA.

19. The isolated polynucleotide of claim 9, wherein said polynucleotide is RNA.

20. A recombinant vector comprising the polynucleotide of claim 16.

21. A recombinant host cell comprising the polynucleotide of claim 16, wherein said polynucleotide is DNA.

22. A method for producing a polypeptide comprising expressing from the recombinant cell of claim 11 the polypeptide encoded by said polynucleotide.

23. A method for producing a polypeptide comprising expressing from the recombinant cell of claim 15 the polypeptide encoded by said polynucleotide.

24. A method for producing a polypeptide comprising expressing from the recombinant cell of claim 18 the polypeptide encoded by said polynucleotide.

25. A method for producing a polypeptide comprising expressing from the recombinant cell of claim 21 the polypeptide encoded by said polynucleotide.

26. An isolated polynucleotide comprising a polynucleotide having at least a 95% identity to a member selected from the group consisting of:

(a) a polynucleotide encoding the same mature polypeptide encoded by the human cDNA in ATCC Deposit No. 75821, and (b) the complement of (a).

27. The isolated polynucleotide of claim 26, wherein the member is (a).

28. The isolated polynucleotide of claim 26 comprising a polynucleotide which encodes the same mature polypeptide encoded by the human cDNA in ATCC Deposit No. 75821.

29. The isolated polynucleotide of claim 26 wherein said polynucleotide comprises DNA identical to the coding portion of the human cDNA in ATCC Deposit No. 75821 which encodes a mature polypeptide.

30. A recombinant host cell comprising the polynucleotide of claim 26, wherein said polynucleotide is the DNA of (a) which codes for the mature C5A receptor protein.

31. A recombinant host cell comprising the polynucleotide of claim 26, wherein said polynucleotide includes the portion of the deposited DNA which codes for the polypeptide having an amino acid sequence according to SEQ ID NO:2.

32. A recombinant host cell comprising the polynucleotide of claim 31, wherein said polynucleotide codes for the mature C5A receptor protein.

33. A method for producing a polypeptide comprising expressing from the recombinant cell of claim 30 the polypeptide encoded by said polynucleotide.

34. A method for producing a polypeptide comprising expressing from the recombinant cell of claim 32 the polypeptide encoded by said polynucleotide.

35. A method for producing a polypeptide comprising expressing from the recombinant cell of claim 31 the polypeptide encoded by said polynucleotide.

* * * * *